United States Patent
Neumann

(10) Patent No.: US 11,318,011 B2
(45) Date of Patent: May 3, 2022

(54) MECHANICALLY EXPANDABLE HEART VALVE WITH LEAFLET CLAMPS

(71) Applicant: Edwards Lifesciences Corporation, Irvine, CA (US)

(72) Inventor: Yair A. Neumann, Moshav Sede Varburg (IL)

(73) Assignee: Edwards Lifesciences Corporation, Irvine, CA (US)

( * ) Notice: Subject to any disclaimer, the term of this patent is extended or adjusted under 35 U.S.C. 154(b) by 399 days.

(21) Appl. No.: 16/389,312

(22) Filed: Apr. 19, 2019

(65) Prior Publication Data

US 2019/0328518 A1    Oct. 31, 2019

Related U.S. Application Data

(60) Provisional application No. 62/663,615, filed on Apr. 27, 2018.

(51) Int. Cl.
*A61F 2/24* (2006.01)

(52) U.S. Cl.
CPC .... *A61F 2/2418* (2013.01); *A61F 2220/0041* (2013.01); *A61F 2220/0091* (2013.01); (Continued)

(58) Field of Classification Search
CPC ........... A61F 2/2418; A61F 2220/0091; A61F 2/2463; A61F 2230/001; A61F 2220/0041; A61F 2230/0054
See application file for complete search history.

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 2246526 A1 | 3/1973 |
| DE | 0144167 C | 6/1985 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Brian E Pellegrino
(74) *Attorney, Agent, or Firm* — Klarquist Sparkman, LLP; Joel B. German

(57) ABSTRACT

A frame for a prosthetic heart valve includes a plurality of strut members arranged to form an annular main body and coupled together by a plurality of pivot joints. The main body of the frame is radially collapsible to a collapsed configuration and radially expandable to an expanded configuration, and the frame has an inflow end and an outflow end. The frame further includes a plurality of leaflet clamps disposed on the exterior of the main body of the frame and coupled to the strut members. The leaflet clamps are movable between an open position corresponding to the collapsed configuration of the frame and a closed position corresponding to the expanded configuration of the frame. Motion of the main body of the frame between the collapsed configuration and the expanded configuration causes corresponding motion of the leaflet clamps between the open position and the closed position.

20 Claims, 12 Drawing Sheets

(52) U.S. Cl.
CPC . *A61F 2230/001* (2013.01); *A61F 2230/0054* (2013.01); *A61F 2230/0069* (2013.01); *A61F 2250/0065* (2013.01)

(56) References Cited

U.S. PATENT DOCUMENTS

| | | | |
|---|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |

(56) References Cited

U.S. PATENT DOCUMENTS

| | | |
|---|---|---|
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Mon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0038405 A1* | 2/2019 | Iamberger ............ A61F 2/2436 623/2.1 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10013815 A1 | 4/2002 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |

(56) References Cited

FOREIGN PATENT DOCUMENTS

| | | |
|---|---|---|
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008029296 A2 | 3/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.

* cited by examiner

MECHANICALLY EXPANDABLE HEART VALVE WITH LEAFLET CLAMPS

CROSS REFERENCE TO RELATED APPLICATION

The present application claims the benefit of U.S. Provisional Application No. 62/663,615, filed on Apr. 27, 2018, which is incorporated herein by reference in its entirety.

FIELD

The present disclosure relates to implantable, mechanically expandable prosthetic devices, such as prosthetic heart valves, and to methods and delivery assemblies for such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on chronically ill patients, with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from heart valve disease such as valve stenosis, valve insufficiency, etc., who are older than 80 years cannot be operated on for valve replacement.

Because of the drawbacks associated with conventional open-heart surgery, percutaneous and minimally-invasive surgical approaches are garnering attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design consideration is the ability of the prosthetic heart valve to remain at the treatment location after deployment without becoming dislodged. In particular, there is a need for improvements to devices and methods for engaging the leaflets of a native heart valve when implanting a prosthetic heart valve.

SUMMARY

Certain embodiments of the disclosure concern frames for prosthetic heart valves including leaflet clamps. In a representative embodiment, a frame for a prosthetic heart valve comprises a plurality of strut members arranged to form an annular main body of the frame and coupled together by a plurality of pivot joints. The main body of the frame is radially collapsible to a collapsed configuration and radially expandable to an expanded configuration, and the main body of the frame has an inflow end and an outflow end. The frame further comprises a plurality of leaflet clamps disposed on an exterior of the main body of the frame and coupled to the strut members. The plurality of leaflet clamps are movable between an open position corresponding to the collapsed configuration of the main body of the frame and a closed position corresponding to the expanded configuration of the main body of the frame. Motion of the main body of the frame between the collapsed configuration and the expanded configuration causes corresponding motion of the leaflet clamps between the open position and the closed position.

In some embodiments, the leaflet clamps comprise a first end portion coupled to the main body of the frame and a free second end portion, and when the leaflet clamps are in the open position, the free second end portions are spaced radially outwardly from the main body of the frame.

In some embodiments, when the leaflet clamps are in the closed position, the free second end portions are disposed adjacent the main body of the frame.

In some embodiments, the strut members have respective inflow end portions located at the inflow end of the main body of the frame, respective outflow end portions located at the outflow end of the main body of the frame, and respective central portions between the inflow end portions and the outflow end portions. When the frame is in the expanded configuration, the central portions of the strut members are offset radially inwardly from the inflow end portions and from the outflow end portions of the strut members relative to a longitudinal axis of the frame such that the main body of the frame has an hourglass-shaped profile.

In some embodiments, when the frame is in the collapsed configuration, the central portions of the strut members are offset radially outwardly from the respective inflow end portions and outflow end portions of the strut members with respect to the longitudinal axis of the frame such that the main body of the frame has a barrel-shaped profile.

In some embodiments, the leaflet clamps each comprise a pair of strut members pivotably coupled to the strut members of the main body of the frame.

In some embodiments, the strut members of the leaflet clamps each comprise a first end portion and a second end portion, and when the leaflet clamps are in the open position, the second end portions of the strut members of the leaflet clamps are spaced radially outwardly from the main body of the frame.

In some embodiments, the second end portions of the strut members of each leaflet clamp are coupled to each other such that the leaflet clamps are V-shaped when the frame is in the expanded configuration.

In some embodiments, the first end portions of the strut members of the leaflet clamps are coupled to apices of the outflow end of the main body of the frame.

In some embodiments, a prosthetic heart valve comprises any of the frame embodiments described herein and a leaflet structure disposed at least partially within the frame.

In another representative embodiment, a frame for a prosthetic heart valve comprises a plurality of strut members arranged to form an annular main body. The main body of the frame is radially collapsible to a collapsed configuration and radially expandable to an expanded configuration, has an inflow end and an outflow end, and defines a longitudinal axis. The strut members of the frame have respective inflow end portions located at the inflow end of the main body, respective outflow end portions located at the outflow end of the main body, and respective central portions between the inflow end portions and the outflow end portions. When the frame is in the expanded configuration, the central portions of the strut members are offset radially inwardly from the inflow end portions and from the outflow end portions of the strut members relative to the longitudinal axis such that the main body of the frame has an hourglass-shaped profile.

In some embodiments, when the main body of the frame is in the collapsed configuration, the central portions of the strut members are offset radially outwardly from the respective inflow end portions and outflow end portions of the strut members with respect to the longitudinal axis of the frame such that the main body of the frame has a barrel-shaped profile.

In some embodiments, the frame further comprises a plurality of leaflet clamps disposed on the exterior of the main body of the frame and coupled to the strut members.

In some embodiments, the leaflet clamps are movable between an open position corresponding to the collapsed configuration of the main body of the frame and a closed position corresponding to the expanded configuration of the main body of the frame.

In some embodiments, the leaflet clamps each comprise a pair of strut members pivotably coupled to the strut members of the main body of the frame.

In some embodiments, the strut members of the leaflet clamps each comprise a first end portion and a second end portion, and when the leaflet clamps are in the open position, the second end portions of the strut members of the leaflet clamps are spaced radially outwardly from the main body of the frame.

In some embodiments, the second end portions of the strut members of each leaflet clamp are coupled to each other such that the leaflet clamps are V-shaped when the frame is in the expanded configuration.

In some embodiments, the leaflet clamps are bowed when the frame is in the expanded configuration.

In some embodiments, the strut members of the main body of the frame are coupled together by a plurality of pivot joints.

In another representative embodiment, a method of implanting a prosthetic heart valve comprises advancing a prosthetic heart valve in a collapsed configuration to a native heart valve using a delivery apparatus. The prosthetic heart valve comprises a plurality of strut members coupled together by a plurality of pivot joints and arranged to form a frame having an annular main body. The main body of the frame is radially collapsible to the collapsed configuration and radially expandable to an expanded configuration, and includes a plurality of leaflet clamps disposed on the exterior of the main body of the frame and coupled to the strut members. The leaflet clamps are movable between an open position corresponding to the collapsed configuration of the main body of the frame and a closed position corresponding to the expanded configuration of the main body of the frame. The method further comprises positioning the prosthetic heart valve such that leaflets of the native heart valve are located between respective leaflet clamps and the main body of the frame, and radially expanding the prosthetic heart valve from the collapsed configuration to the expanded configuration such that the leaflet clamps move from the open position to the closed position and clamp the leaflets against the prosthetic heart valve.

In some embodiments, the leaflet clamps comprise first end portions coupled to an outflow end of the main body of the frame and free second end portions, and radially expanding the prosthetic heart valve further comprises expanding the main body of the frame beyond a natural diameter of the strut members such that the outflow end of the main body of the frame moves radially outwardly of a central portion of the main body of the frame and the free second end portions of the leaflet clamps move adjacent the main body of the frame.

The foregoing and other objects, features, and advantages of the disclosed technology will become more apparent from the following detailed description, which proceeds with reference to the accompanying figures.

DETAILED DESCRIPTION

Figure 1:
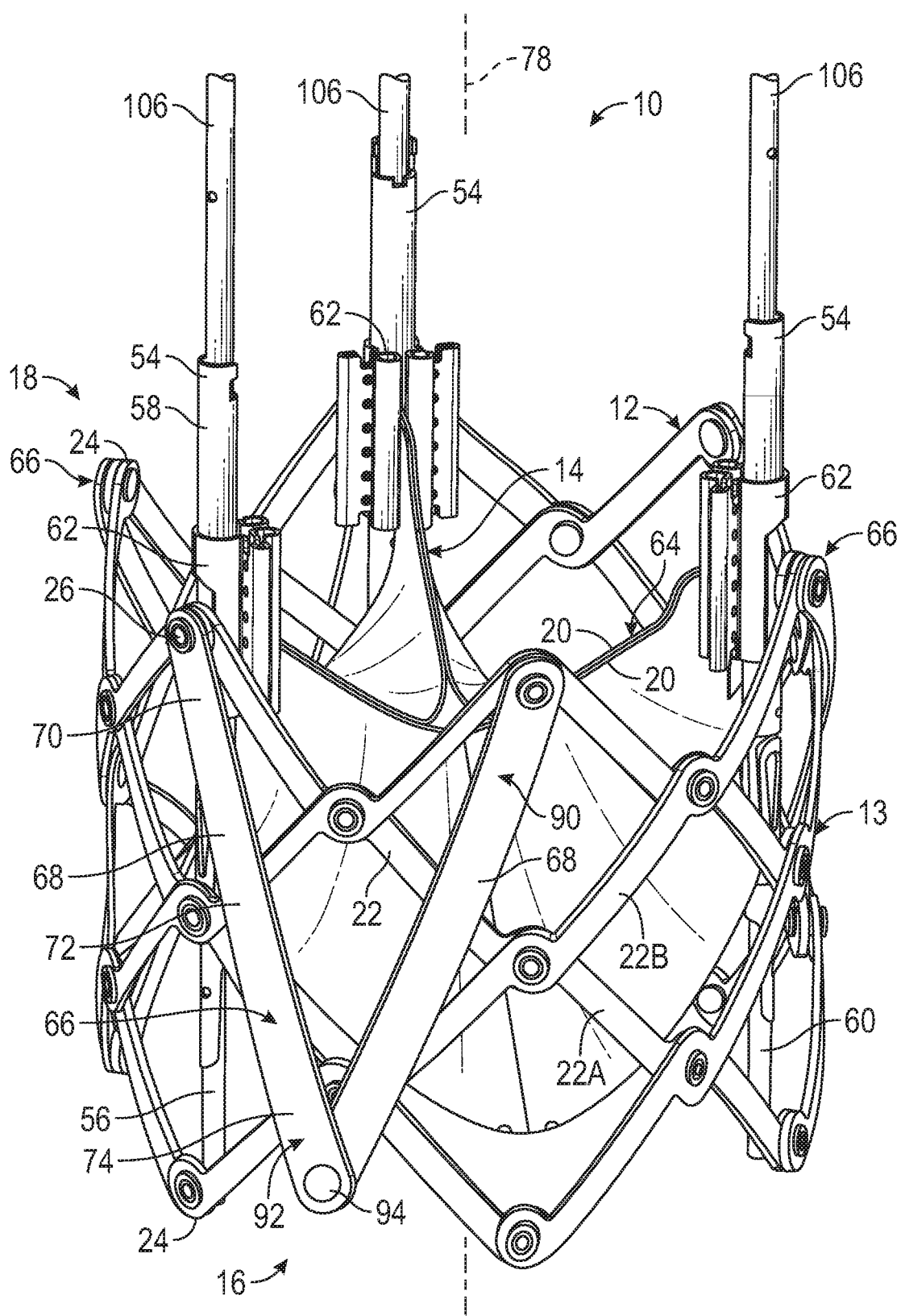
FIG. 1 is a perspective view illustrating a representative embodiment of a prosthetic heart valve including a mechanically expandable frame having a plurality of leaflet clamps.

The present disclosure concerns embodiments of implantable prosthetic devices and, in particular, implantable prosthetic valves, and methods for implanting such devices. In particular embodiments, the prosthetic device comprises a prosthetic heart valve, and can be configured to be implanted in any of the native heart valves (aortic, mitral, pulmonary, and tricuspid). In addition, the prosthetic heart valve can be, for example, a transcatheter heart valve, a surgical heart valve, or a minimally-invasive heart valve. The prosthetic valve also can comprise other types of valves implantable within other body lumens outside of the heart, or heart valves that are implantable within the heart at locations other than the native valves, such as trans-atrial or trans-ventricle septum valves.

The disclosed prosthetic heart valves are particularly suited for implantation in the native aortic valve. In the context of a prosthetic aortic valve, the terms "lower" and "upper" are used interchangeably with the terms "inflow" and "outflow", respectively, for convenience. Thus, for example, the lower end of the prosthetic valve is its inflow end and the upper end of the prosthetic valve is its outflow end in the orientation shown in the drawings. However, it should be understood that the prosthetic valve can be implanted in the reverse orientation. For example, for implantation at the mitral valve position, the upper end of the prosthetic valve is the inflow end and the lower end of the valve is the outflow end.

In some embodiments, the prosthetic valves described herein can include docking mechanisms configured as leaflet clamps to clamp the leaflets of a native heart valve against the prosthetic heart valve. In certain configurations, the leaflet clamps can be movable between an open configuration corresponding to a radially collapsed configuration of the prosthetic valve, and a closed configuration corresponding to a radially expanded configuration of the prosthetic valve. In some embodiments, the diameter of the frame of the prosthetic valve can vary along a longitudinal axis of the frame. The diameter of various parts of the frame can also vary between the collapsed configuration and the expanded configuration. For example, in certain configurations, the inflow and outflow ends of the frame can be disposed radially inwardly of the central portion of the frame when the frame is in the collapsed configuration such that the frame has a convex or barrel-shaped profile. Conversely, when the frame is in the expanded configuration, the central portion of the frame can be disposed radially inwardly of the inflow and outflow ends of the frame such that the frame exhibits a concave or hourglass-shaped outer profile. When the leaflet clamps are coupled to the frame, this radial motion of the inflow and outflow ends of the frame relative to the central portion of the frame can be used to actuate the leaflet clamps between an open position, in which a leaflet-receiving space is defined between the leaflet clamps and the frame, and a closed position, in which the leaflet clamps are disposed against or adjacent the frame.

For example, FIG. 1 illustrates a representative embodiment of a prosthetic heart valve 10. The prosthetic valve 10 can include a mechanically expandable stent or frame 12 having an annular main body 13, and a leaflet structure 14 situated within and coupled to the frame 12. The frame 12 can include an inflow end 16 and an outflow end 18. The leaflet structure can comprise a plurality of leaflets 20, such as three leaflets arranged to collapse in a tricuspid arrangement similar to the aortic valve. Alternatively, the prosthetic valve can include two leaflets 20 configured to collapse in a bicuspid arrangement similar to the mitral valve, or more than three leaflets, depending upon the particular application. The prosthetic valve 10 can also include one or more sealing members to help seal the prosthetic valve against surrounding tissue once implanted. A sealing member can take the form of, for example, an annular skirt formed from a suitable fabric (e.g., PET) or natural tissue (e.g., pericardial tissue). The prosthetic valve can include an annular skirt on the inner surface of the frame 12 and/or the outer surface of the frame 12.

The frame 12 can include a plurality of interconnected strut members 22 (also referred to as "first strut members") arranged in a lattice-type pattern and forming a plurality of apices 24 at the inflow and outflow ends 16, 18 of the main body 13 of the prosthetic valve. In the illustrated configuration, the frame 12 includes a first set of strut members 22A and a second set of strut members 22B. The strut members 22A of the first set are located radially inward of the strut members 22B of the second set such that the strut members 22B are on the outside of the frame. In the illustrated example, the strut members 22A can be angled in a first direction, and can extend helically about a longitudinal axis 78 of the frame 12, while the strut members 22B can be angled in the opposite direction to the strut members 22A, and can extend helically about the longitudinal axis 78 in a direction opposite to the helicity of the strut members 22A.

Figure 2:
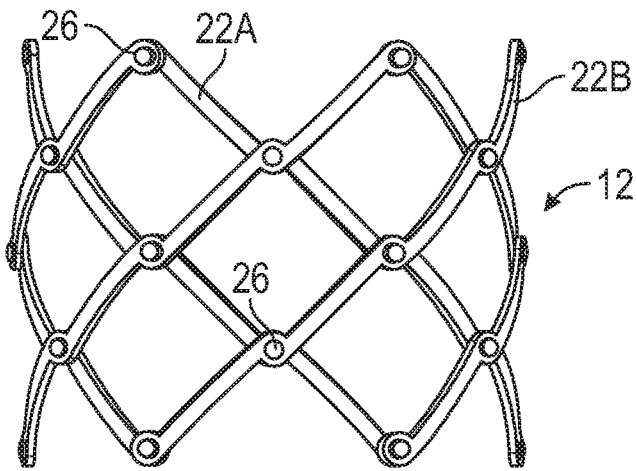
FIG. 2 is a side elevation view of the frame of the prosthetic heart valve of FIG. 1.
Figure 3:
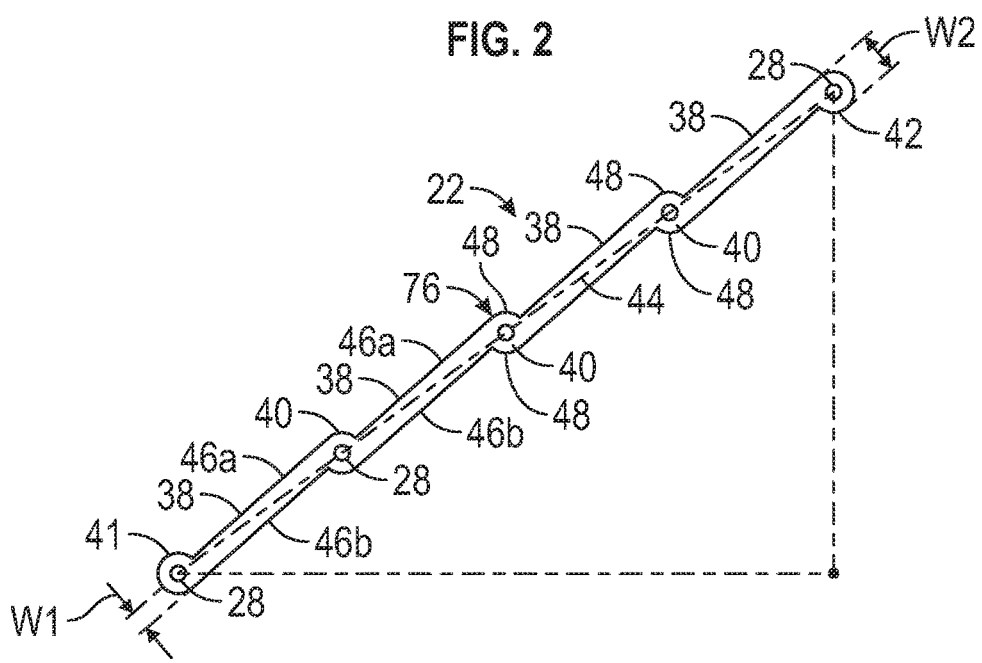
FIG. 3 is a perspective view of a representative embodiment of a strut member.

FIG. 2 illustrates a representative embodiment of the frame 12 of the prosthetic valve 10 without the valvular structure for purposes of illustration, and FIG. 3 illustrates a representative embodiment of a strut member 22 in greater detail. With reference to FIG. 3, the strut members 22 can define a plurality of openings 28 spaced apart along the lengths of the strut members. For example, in the illustrated embodiment, the strut members 22A and 22B can define openings 28 at locations along their lengths where the strut members 22A of the first set overlap the strut members 22B of the second set. The strut members 22 can also include openings 28 defined at their respective end portions such that respective strut members 22A and 22B can be coupled together to form the apices 24 at the inflow and outflow ends of the frame.

As shown in FIG. 3, each strut member 22 can have an offset, or zig-zag, pattern defined by a plurality of offset linear portions or segments 38. The linear segments 38 in the illustrated embodiment are arranged end-to-end relative to each other with adjacent ends interconnected to each other by intermediate segments 40. The strut 22 can have enlarged first end portions 41 at the inflow end of the frame and second end portions 42 at the outflow end of the frame. Thus, the first and second end portions 41, 42 can form the apices 24 at the inflow and outflow ends of the frame. The strut members 22 can also include central portions 76 located midway between the first and second end portions 41, 42.

Figure 4A:
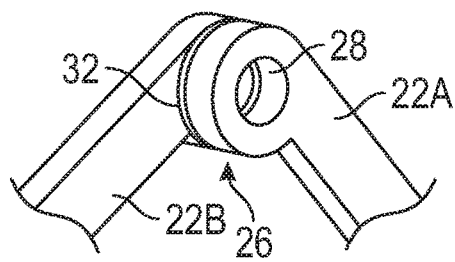
FIG. 4A is a perspective view of a representative embodiment of a pivot joint.
Figure 4B:
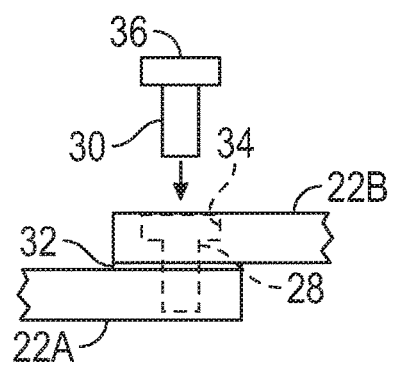
FIG. 4B is a top plan view of the pivot joint of FIG. 4A.

Each linear segment 38 can be slightly laterally offset from an adjacent linear segment 38 in a direction perpendicular to the overall length of the strut 22 to provide the zig-zag pattern to the strut. Each of the intermediate segments 40 and end portions 41 and 42 can have a respective opening 28 at its geometric center for receiving a fastener 30 (FIG. 4B). The amount of offset of each linear segment 38 relative to an adjacent linear segment along the length of the strut 22 can be constant such that an axis 44 can pass through the aperture 28 of each intermediate segment 40 along the entire length of the strut. In alternative embodiments, the amount of offset between two adjacent linear segments 38 can vary along the length of the strut. For example, the amount of offset between linear segments 38 adjacent the outflow end of the frame can be greater than the amount of offset between linear segments 38 adjacent the inflow end of the frame, or vice versa.

The linear segments 38 can include at least substantially flat or linear opposing longitudinal edges 46a, 46b extending between curved or rounded edges 48 of the intermediate segments 40. In alternative embodiments, the opposing edges 48 of the intermediate segments 40 can be substantially flat or linear edges that extend at an angle between respective ends of the edges 46a, 46b of the liner segments 38.

As best shown in FIG. 3, the width W1 of each liner segment 38 is defined as the distance measured between the opposing edges 46a and 46b of a segment 38. In the illustrated embodiment, the width W1 is constant along the length of the strut 22. As such, each longitudinal edge 46a is laterally offset from an adjacent longitudinal edge 46a of an adjacent linear segment 38, and each longitudinal edge 46b is laterally offset from an adjacent longitudinal edge 46b of an adjacent linear segment 38. The width W2 of each intermediate segment 40 and end portion 41, 42 can be greater than the width W1 of the linear segments 38.

In alternative embodiments, the width W1 of each linear segment 38 can vary along the length of a strut. For example, the width W1 of a linear segment 38 adjacent the inflow end of the frame can be greater than the width W1 of a linear segment 38 adjacent the outflow end of the frame, or vice versa. Further, where the widths W1 of the linear segments 38 vary along the length of a strut 22, a linear segment can have one longitudinal edge 46a or 46b that is collinear with a longitudinal edge of an adjacent linear segment on the same side of the strut, while the other longitudinal edge 46a, 46b is laterally offset from the longitudinal edge of an adjacent linear strut on the same side of the strut. In other words, the strut 22 can have an overall zig-zag or offset pattern by virtue of the varying widths W1 of the linear segments.

In alternative embodiments, the struts 22 can have linear segments 38 that are not offset from each other; that is, the struts are substantially rectangular with longitudinal sides of each strut extending continuously from one end of the strut to the opposite end of the strut without offset portions (e.g., similar to struts 68, described below)

Returning to FIGS. 1 and 2, the strut members 22A of the first set of strut members can be pivotably coupled to the strut members 22B of the second set of strut members by hinges or joints 26. In certain examples, the joints 26 can be formed by inserting fasteners 30 (e.g., rivets, pins, etc.) through the openings 28 where the strut members overlap, including at the apices 24. FIGS. 4A and 4B illustrate a representative joint 26 in greater detail. Referring to FIG. 4A, a spacer 32, such as a washer or bushing, can be disposed in a joint between respective strut members 22A and 22B. The spacers 32 can assist the strut members 22A and 22B in moving relative to one another to expand and/or collapse the frame. The spacers 32 can also act to space the strut members 22A, 22B from one another. In other implementations, the joints 26 need not include spacers 32, and/or the strut members 22 can be spaced apart in a different manner. Referring to FIG. 4B, in particular embodiments, the fasteners 30 do not extend radially outwardly from the openings 28 in the strut members and can be contained completely within the openings. For example, each of the openings 28 on the radially outermost struts 22B can include a counter-bore or enlarged recessed portion 34 that is sized to receive the head portion 36 of a respective fastener 30 (e.g., a rivet). The head portion 36 can be received entirely within the counter-bore 34 and does not extend radially outwardly from the counter-bore. For example, the head portion 36 can be flush with the outer surface of the strut 22B. In this manner, the fasteners 30 do not increase or contribute to the overall crimp profile of the prosthetic valve and do not interfere with or place undue stresses on a delivery sheath in which the valve may be disposed during delivery.

The joints 26 can allow the strut members 22A to pivot relative to the strut members 22B as the frame 12 is expanded or contracted, such as during assembly, preparation, or implantation of the prosthetic valve 10. For example, the frame 12 (and thus the prosthetic valve 10) can be manipulated into a radially compressed or contracted configuration (see FIG. 5) and inserted into a patient for implantation. Once inside the body, the prosthetic valve 10 can be manipulated into an expanded state (FIG. 1) and then released from a delivery apparatus, as further described below.

Figure 5:
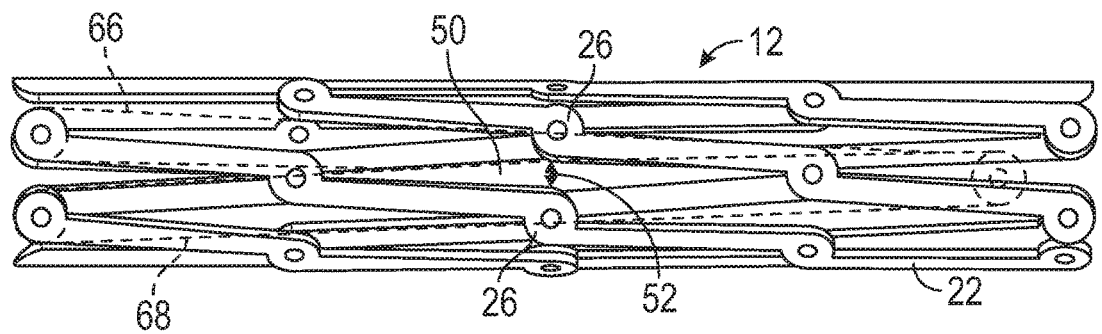
FIG. 5 is a side elevation view of the frame of FIG. 2 in a radially collapsed configuration.

The frame 12 can be configured to protect the soft components (e.g., the leaflets 20, and any skirts, sutures, etc., that form part of the prosthetic valve) from being pinched or cut by the frame during crimping and expansion of the prosthetic valve. For example, FIG. 5 illustrates the frame 12 of FIG. 1 in a radially collapsed configuration. The offset, or zig-zag, pattern of the strut segments 38 can help space apart the struts 22 in the circumferential direction when the frame 12 is in a radially compressed state. As shown, the open lattice structure of the frame 12 defining open cells 50 between the struts 22 can be preserved even when the frame 12 is fully compressed or contracted. For example, with reference to FIG. 5, although the width of the cells 50 along the length of the frame 12 can vary between adjacent struts, a gap 52 remains at the middle of a cell 50 between two adjacent pivot joints 26. The spaced-apart nature of the struts 22, including the gaps 52, can assist in protecting the soft components of the prosthetic valve as the frame 12 is expanded and contracted. The gaps 52 created by the offset configuration of the struts 22 can protect the leaflets 20, a skirt such as a paravalvular leakage skirt (not shown), and/or sutures from being pinched or sheared between adjacent struts 22 when the prosthetic valve is radially compressed. In this manner, the soft components of the prosthetic valve are protected against damage that can occur from contact with the metal struts of the frame.

Returning to FIG. 1, the frame 12 can comprise a plurality of post members 54. In the illustrated configuration, the post members 54 are configured as actuator components that can also function as release-and-locking units (also referred to as locking assemblies or expansion units) configured to radially expand and contract the frame, and to retain the frame in a desired expanded state. In the illustrated configuration, the frame 12 can comprise three actuator components 54 coupled to the frame 12 at circumferentially spaced locations, although the frame may include more or fewer actuator components depending upon the particular application. Each of the actuator components 54 generally can comprise an inner member 56, such as an inner tubular member, and an outer member 58, such as an outer tubular member concentrically disposed about the inner member 56. The inner members 56 and the outer members 58 can be moveable longitudinally relative to each other in a telescoping manner to radially expand and contract the frame 12, as further described in U.S. Publication No. 2018/0153689, which is incorporated herein by reference.

In the illustrated configuration, the inner members 56 can have distal end portions 60 coupled to the inflow end 16 of the frame 12 (e.g., with a coupling element such as a pin member). In the illustrated embodiment, each of the inner members 56 is coupled to the frame at respective apices 24 at the inflow end 16 of the frame. The outer members 58 can be coupled to apices 24 at the outflow end 18 of the frame 12 at, for example, a mid-portion of the outer member, as shown in FIG. 1, or at a proximal end portion of the outer member, depending upon the particular application.

The inner member 56 and the outer member 58 can telescope relative to each other between a fully contracted state (corresponding to a fully radially expanded state of the prosthetic valve) and a fully extended state (corresponding to a fully radially compressed state of the prosthetic valve). In the fully extended state, the inner member 56 is fully extended from the outer member 58. In this manner, the actuator components 54 allow the prosthetic valve to be fully expanded or partially expanded to different diameters inside a patient's body and retain the prosthetic valve in the partially or fully expanded state. The inner and outer members 56, 58 have respective locking elements that are configured to engage each other and prevent radial compression of the frame when the frame is expanded to a desired expanded diameter and the locking elements are actuated by a user, as further disclosed in U.S. Publication No. 2018/0153689.

The prosthetic valve 10 can include various other types of actuators and/or locking devices for controlling radial expansion of the valve and/or retaining the valve in an expanded state. In some embodiments, for example, the actuator components 54 can be screw actuators configured to radially expand and collapse the frame 12 by rotation of one of the components of the actuators. For example, the inner members 56 can be configured as screws having external threads that engage internal threads of corresponding outer components. In some embodiments, the internal friction or resistance of the screws within the screw actuators can be sufficient to retain the frame in a desired expanded state. Further details regarding screw actuators and various other types of actuators and locking devices that can be incorporated in the prosthetic valve are disclosed in: U.S. Patent Publication No. 2018/0153689; U.S. Application Ser. No. 16/105,353, filed Aug. 20, 2018; and U.S. Publication No. 2014/0296962, all of which documents are incorporated herein by reference.

Still referring to FIG. 1, the prosthetic valve 10 can include a plurality of commissure support elements configured as commissure clasps or clamps 62. The adjacent side portions of the leaflets are arranged in pairs forming a plurality of commissures 64 of the leaflets. In the illustrated configuration, the prosthetic valve includes a commissure clamp 62 positioned at each commissure 64 and configured to grip two adjacent side portions of adjacent leaflets 20 of the commissures at a location spaced radially inwardly of the frame 12.

Referring to FIG. 1, the prosthetic valve 10 can include a plurality of docking mechanisms or retention mechanisms configured as leaflet clamps 66. In the illustrated embodiment, the leaflet clamps 66 are disposed on the radially outward aspect of the main body 13 of the frame 12, and can be configured to clamp onto, grip, or clip native leaflets of a heart valve into which the prosthetic valve 10 is implanted such that the prosthetic heart valve is retained in the annulus after deployment. In certain embodiments, each leaflet clamp 66 can include a first end portion 90 coupled to the main body 13 (e.g., at the outflow end 18), and a second end portion 92. In some embodiments, the second end portion 92 can be a free end portion that is not directly connected to the main body 13, and which can be movable (e.g., movable radially inwardly and outwardly) relative to the main body of the frame as the frame expands and/or contracts.

In the illustrated embodiment, the prosthetic valve 10 includes three clamps 66, although a greater or fewer number may be used. The clamps 66 are desirably, although not necessarily, equally angularly spaced around the circumference of the main body of the frame. When intended to be implanted within a native valve having three leaflets (e.g., the aortic valve), the prosthetic valve 10 can have three clamps 66, with each clamp being positioned to clamp onto one of the native leaflets. When intended to be implanted within a native valve having two leaflets (e.g., the mitral valve), the prosthetic valve 10 can have two clamps 66, with each clamp being positioned to clamp onto one of the native leaflets. In other embodiments, the prosthetic valve 10 can have a number of clamps 66 that does not equal the number of native leaflets of the native valve in which the prosthetic valve 10 is to be implanted and/or the prosthetic valve 10 can have more than one clamp that is positioned to clamp onto a single native leaflet.

In the illustrated embodiment, each leaflet clamp 66 can comprise a pair of strut members 68 (also referred to as "second strut members"). The strut members 68 can include respective first end portions 70, central portions 72, and second end portions 74. The first end portions 70 can be coupled to the main body 13 of the frame 12. More particularly, in certain embodiments, the first end portions 70 of the strut members 68 can be pivotably coupled to adjacent apices 24 (e.g., with the pivot joints 26) at the outflow end 18 of the frame. The second end portions 74 of the strut members 68 of each clamp 66 can be pivotably coupled to each other by a pivot joint 94. In this manner, the leaflet clamps 66 can be movable between an expanded configuration (FIG. 1) and a collapsed configuration (shown in dashed lines in FIG. 5) corresponding to the expanded and collapsed configurations of the frame 12.

For example, when the prosthetic valve 10 is in the expanded configuration, the leaflet clamps 66 are also in the expanded configuration, and the first end portions 70 of the strut members 68 are circumferentially spaced apart from each other around the frame 12 such that the strut members 68 form a V-shape. In the illustrated embodiment, the opening of the V is oriented toward the outflow end of the frame. When the prosthetic valve 10 is moved to the collapsed configuration, the leaflet clamps 66 can move to the collapsed configuration as well. For example, the first end portions 70 of the strut members 68 can pivot about the pivot joints 26 such that the first end portions 70 move closer together as the frame 12 is radially collapsed to the configuration shown in FIG. 5. The strut members 68 of the leaflet clamps 66 can also form a V-shape when the leaflet clamps are in the collapsed configuration, as shown in dashed lines in FIG. 5, but with the first end portions 70 of the strut members located closer together than in the expanded configuration.

In certain embodiments, the main body 13 of the frame 12 can be configured such that it has a barrel-shaped profile when in the collapsed configuration, and an hourglass-shaped profile when in the expanded configuration. As used herein, the term "barrel-shaped profile" means that a central portion 80 of the main body 13 of the frame 12 is offset radially outwardly from the inflow end 16 and the outflow end 18 with respect to a longitudinal axis 78 of the main body of the frame 12 such that a diameter of the central portion of the main body is greater than the diameters of the inflow and outflow ends of the main body. As used herein, the term "hourglass-shaped profile" means that the central portion 80 of the main body 13 is offset radially inwardly from the inflow end 16 and from the outflow end 18 of the frame relative to the longitudinal axis 78 such that the diameter of the central portion of the main body is less than the diameters of the inflow and outflow ends of the main body.

Figure 6:
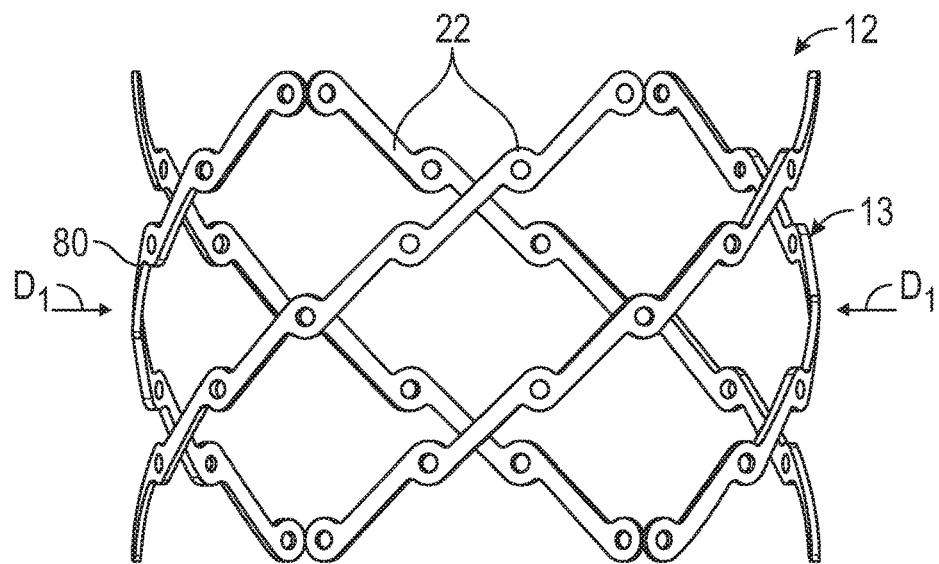
FIG. 6 is a side elevation view of one set of strut members of the frame of FIG. 2 in which the strut members are arranged in the shape of a prosthetic heart valve at a natural diameter of the strut members.
Figure 7:
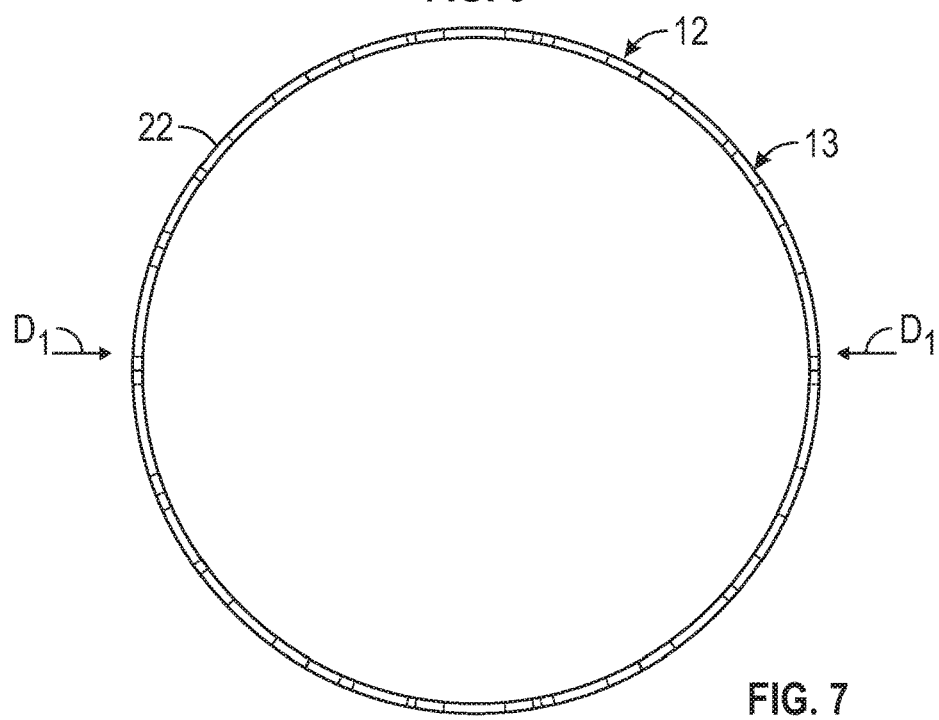
FIG. 7 is a top plan view of the strut members of FIG. 6.

For example, FIGS. 6 and 7 illustrate a single set of strut members 22 (e.g., the outer strut members 22B) of another embodiment of the frame 12 in which the struts comprise seven round segments 40 (including the end portions 41 and 42), and corresponding openings 28. The frame 12 is shown without the leaflet clamps 66 for purposes of illustration. In certain embodiments, the strut members 22 can be cut (e.g., laser cut) from a tube such that the strut members are curved, and have a radius corresponding to a radius of the tube from which the struts were cut. Thus, the main body 13 has a "natural" diameter $D_1$ corresponding to the diameter of the tube from which the strut members 22 were cut. In other embodiments, the strut members 22 can be cut from sheet stock and bent to the desired curvature. In certain embodiments, the strut members 68 of the leaflet clamps 66 can also be cut from one or more tubes such that the strut members are curved to a natural diameter of the tube from which the struts were cut. The natural diameter of the strut members 68 may be larger, the same, or smaller than the natural diameter $D_1$ of the strut members 22, depending upon the particular configuration.

Figure 8:
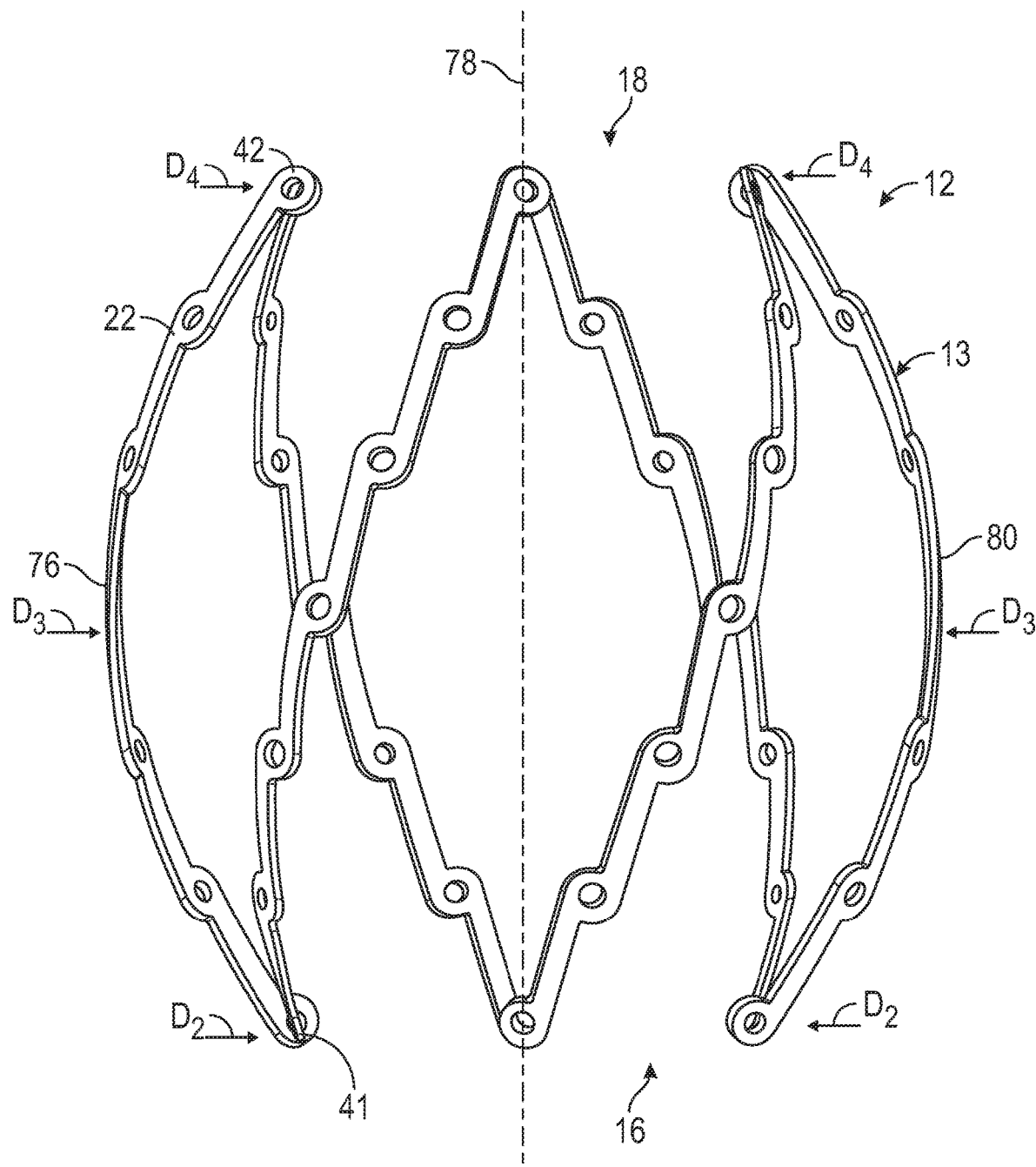
FIG. 8 is a side elevation view illustrating a position of the strut members of FIG. 6 when the frame of FIG. 2 is radially collapsed to a diameter that is less than the natural diameter of the strut members.

When the prosthetic valve 10 is crimped to the radially collapsed configuration, which is less than the natural diameter $D_1$ of the main body of the frame, the central portions 76 of the strut members 22 can tend to bow radially outwardly such that the main body 13 of the frame 12 has a barrel-shaped profile, as shown in FIG. 8. More specifically, as the diameter of the main body 13 is reduced, the first end portions 41 and the second end portions 42 can be positioned radially inwardly of the central portions 76 of the strut members 22 such that the first and second end portions 41, 42 are located closer to the longitudinal axis 78 of the frame than the central portions 76 of the strut members. In this manner, a diameter $D_2$ of the inflow end 16 of the main body 13 and a diameter $D_4$ of the outflow end 18 of the main body can be smaller than a diameter $D_3$ of the central portion 80 of the main body. In other words, the first and second end portions 41, 42 of the strut members 22 can be located radially inwardly of the central portions 76 such that a concave side of the strut members is oriented toward the axis 78 when the diameter of the main body of the frame 12 is reduced below its natural diameter $D_1$. A convex side of the strut members can be oriented away from the axis 78 when the diameter of the main body of the frame 12 is reduced below its natural diameter $D_1$.

Figure 9:
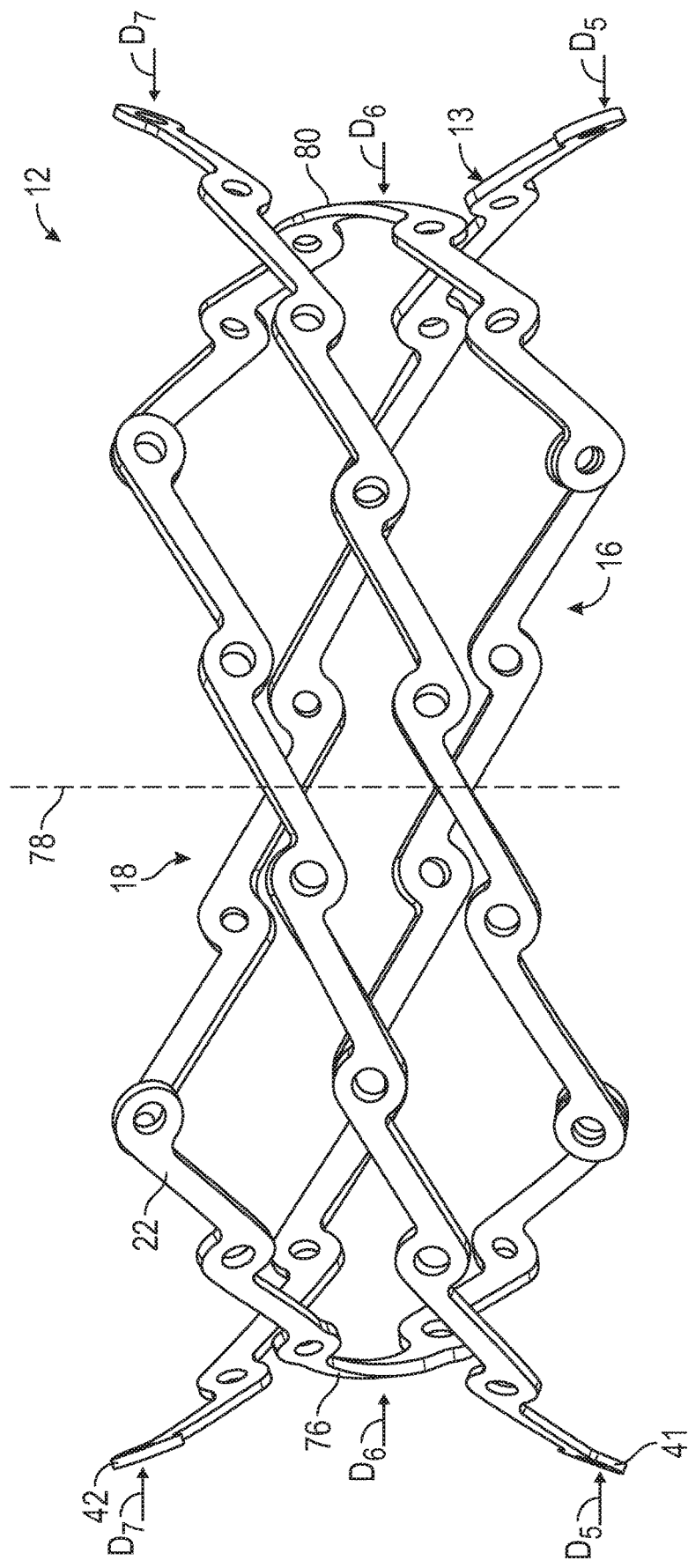
FIG. 9 is a side elevation view illustrating a position of the strut members of FIG. 6 when the frame of FIG. 2 is radially expanded to a diameter that is larger than the natural diameter of the strut members.

Conversely, when the prosthetic valve 10 is expanded to the expanded configuration, the main body 13 can be expanded beyond its natural diameter $D_1$ such that the frame has an hourglass-shaped profile, as shown in FIG. 9. With reference to FIG. 9, the first end portions 41 and the second end portions 42 of the strut members 22 can be positioned radially outwardly of the central portions 76 of the strut members 22 such that the first and second end portions 41, 42 are located farther away from the longitudinal axis 78 of the frame than the central portions 76 of the strut members. In this manner, a diameter $D_5$ of the inflow end 16 of the main body 13 and a diameter $D_7$ of the outflow end 18 of the main body can be smaller than a diameter $D_6$ of the central portion 80 of the main body. In other words, although a concave side of the strut members 22 is still oriented toward the axis 78, the first and second end portions 41, 42 of the strut members 22 can be located radially outwardly of the central portions 76 when the diameter of the main body 13 is expanded beyond its natural diameter $D_1$.

The fully assembled frame 12 including both the inner and outer sets of strut members 22A and 22B can exhibit the shapes described above when in the collapsed and expanded configurations, although the degree of the barrel-shaped profile and the hourglass-shaped profile achieved can vary due to constraints imposed by the joints 26 and the opposite helicity of the inner and outer sets of strut members 22A and 22B. In one representative example, the natural diameter $D_1$ of the main body of the frame can be from 13 mm to 16 mm. Thus, when the frame is crimped to the collapsed configuration, the diameter $D_3$ of the central portion 80 of the main body 13 can be 6 mm. When expanded to the functional size, the main body 13 can be expanded beyond its natural diameter to achieve the hourglass shape. In the above example, the diameter $D_6$ of the central portion 80 of the main body 13 can be 24 mm to 26 mm at its functional size. As shown in FIGS. 8 and 9, a length dimension of the frame 12 (e.g., in the direction of axis 78) can also shorten as the frame is expanded.

Figure 10:
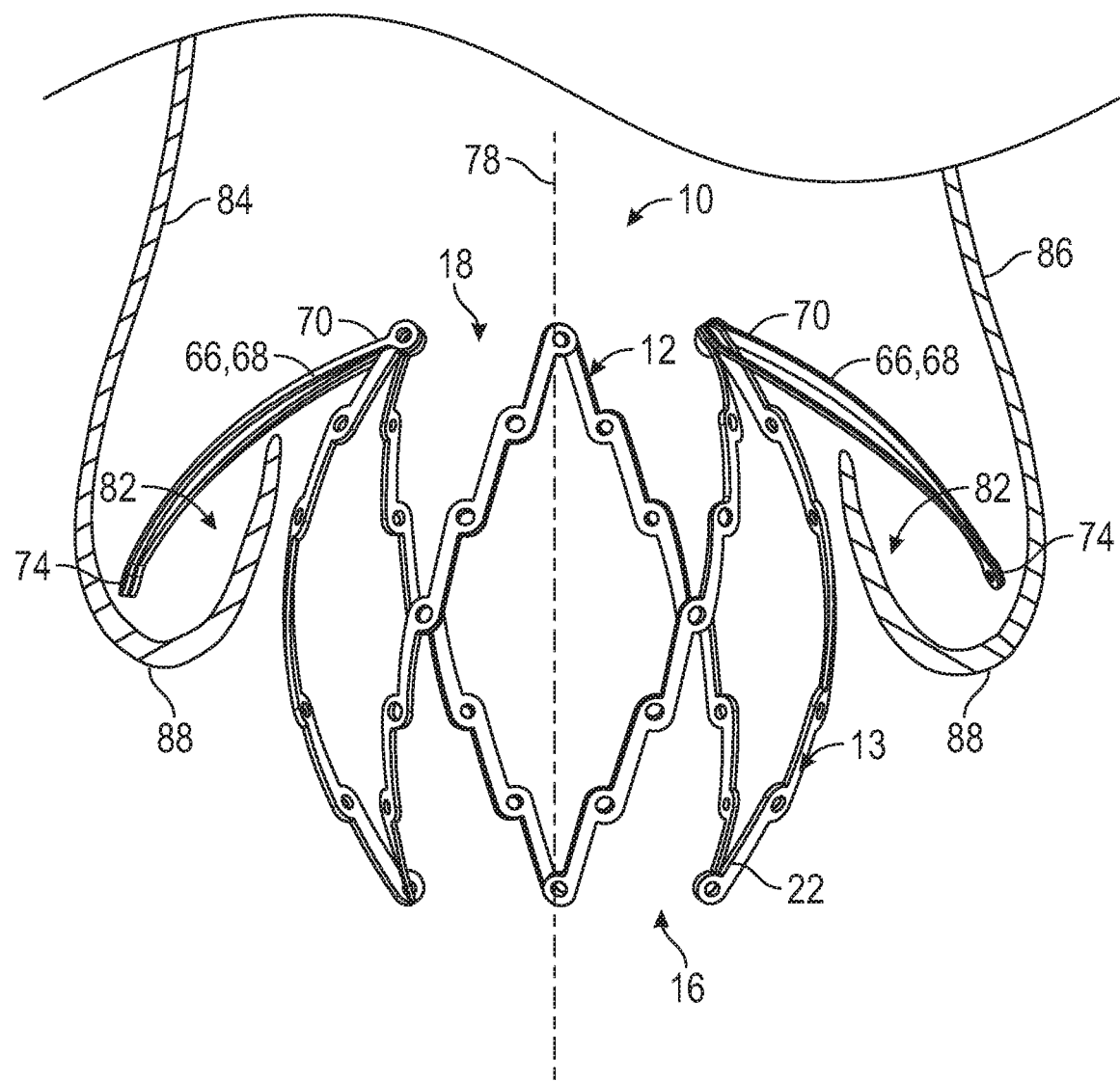
FIG. 10 is a side elevation view illustrating the strut members of FIG. 6 in a collapsed configuration in a native aortic valve, and including leaflet clamps in an open configuration.

The variation in the radial position of the inflow and outflow ends 16, 18 of the main body of the frame 12 with respect to the central portion 80 can be utilized to move or actuate the leaflet clamps 66 between the open and closed positions. For example, FIG. 10 illustrates the frame 12 in a partially radially collapsed configuration in a native heart valve 86 in which the main body of the frame has a barrel-shaped profile. As in FIGS. 6-9 above, only one set of strut members 22 (e.g., the outer strut members 22B) is shown for ease of illustration, although in practice the frame can include both the inner and outer strut members shown in FIG. 1. In the position shown in FIG. 10, because the first end portions 70 of the strut members 68 of the leaflet clamps 66 are coupled to the outflow end 18 of the main body 13, the second end portions 74 of the strut members 68 can be located radially outwardly of the first end portions 70. In this manner, the leaflet clamps 66 can define respective leaflet-receiving regions 82 between the strut members 68 and the main body 13 of the frame 12. The leaflet-receiving regions 82 can be configured to receive leaflets 88 of the native heart valve 86 during implantation. The strut members 68 can also be bowed or curved such that a concave side of the leaflet clamps 66 is oriented radially inwardly toward the central axis 78, and a convex side of the leaflet clamps is oriented radially outward away from the central axis.

Figure 11:
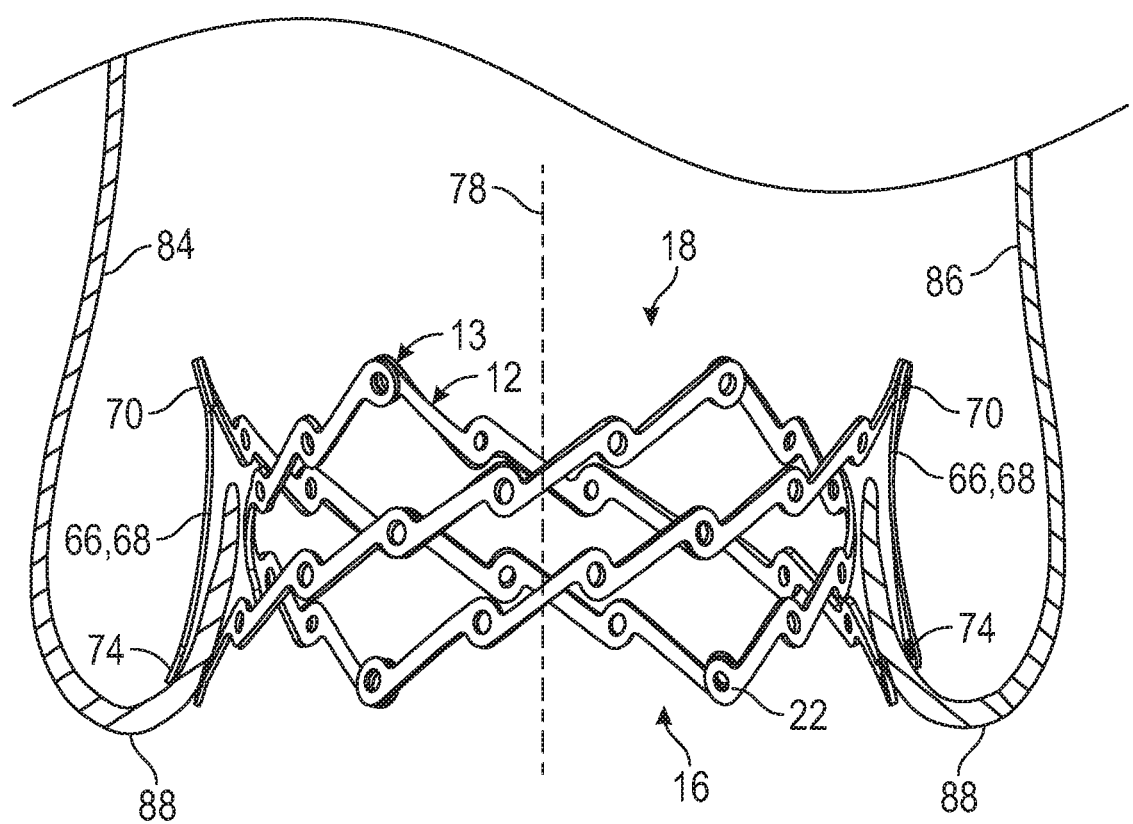
FIG. 11 is a side elevation view illustrating the strut members of FIG. 6 in an expanded configuration such that the leaflet clamps are in the closed configuration and engage native leaflets of the aortic valve.

Conversely, when the prosthetic valve 10 is expanded to its functional size, the main body 13 of the frame 12 can assume the hourglass-shaped profile illustrated in FIG. 11. As described above, as the frame 12 is expanded, the strut members 22 can bow or curve such that the first and second end portions 41, 42 (FIG. 9) of the strut members 22 are positioned radially outwardly of the central portions 76. This can cause the leaflet clamps 66 to move (e.g., by pivoting) to the closed position in which the first end portions 70 of the strut members 68 are located at substantially the same radial distance from the axis 78 as the second end portions 74, or radially outward of the second end portions 74. In the closed position, the second end portions 74 can be adjacent or contacting the main body 13 of the frame 12. In this manner, the leaflet clamps 66 can clamp, grip, or clip the native leaflets 88 of heart valve 86 against the outer strut members 22B of the frame 12 and the inner surfaces of the clamps 66.

As shown in FIG. 11, in the radially expanded configuration of the frame in which the clamps are in the closed position, the strut members 68 of the clamps can be slightly bowed to match the shape of the main body of the frame such that the first and second end portions 70, 74 are located radially outwardly of the central portions of the strut members 68. Stated differently, the concavity of the strut members 68 can be reversed as compared to the open position shown in FIG. 10 such that a concave side of the leaflet clamps 66 is oriented away from the center axis 78, and a convex side of the clamps is oriented radially inward toward the main body and the center axis.

The strut members 22 and/or the strut members 68 can be made from any of various biocompatible materials. For example, in certain embodiments, the strut members 22 and/or the strut members 68 can be made from any of various metal alloys, including nickel titanium alloys such as nitinol, or stainless steel, etc.

Figure 12:
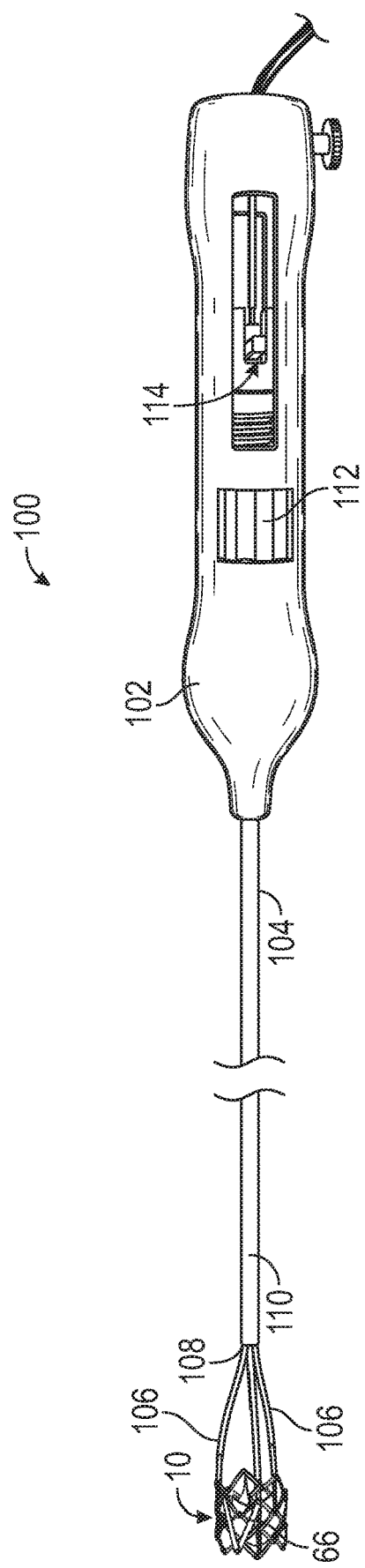
FIG. 12 is a perspective view of a representative embodiment of a delivery apparatus.

The disclosed prosthetic valve embodiments can be radially collapsed and delivered to the heart percutaneously using any of a variety of delivery systems. For example, FIG. 12 shows a representative example of a delivery assembly 100 configured for use with the prosthetic valve 10 of FIGS. 1-11 and described in detail in U.S. Publication No. 2018/0153689 incorporated by reference above. The delivery assembly 100 can include a handle 102, an elongate shaft 104 extending distally from the handle 102, and a plurality of first actuation members 106 (e.g., in the form of positioning tubes) extending through the shaft and distally outwardly from a distal end 108 of the shaft 104. The first actuation members 106 can be coupled to respective expansion units 54 of the valve frame 12.

The delivery assembly 100 can include second actuation members (not shown) that extend co-axially through the first actuation members and are connected to respective inner members 56. To produce radial expansion of the prosthetic valve, the first actuation members 106 are actuated to apply a distally directed force to the frame 12 and/or the second actuation members are actuated to apply a proximally directed force to the inner members 56. To produce radial compression of the prosthetic valve, the first actuation members 106 are actuated to apply a proximally directed force to the frame 12 and/or the second actuation members are actuated to apply a distally directed force to the inner members 56.

Initially, the prosthetic valve 10 can be in a radially collapsed configuration within a sheath 110 of the shaft 104. The sheath 110 retains the clamps 66 against the outer surface of the frame 12 during delivery of the prosthetic valve. When the distal end of the delivery apparatus has been advanced through the patient's vasculature to the treatment site (e.g., at the ascending aorta), the prosthetic valve 10 can be advanced from the sheath 110, such as by using a rotatable actuator 112 on the handle 102. The clamps desirably have sufficient elasticity such that when the prosthetic valve is deployed from the sheath, the clamps 66 can automatically self-expand away from the frame 12 to their open positions shown in FIG. 10. The prosthetic valve 10 can then be positioned at the treatment site, expanded, and deployed using a release assembly generally indicated at 114. For example, returning to FIGS. 10 and 11, the prosthetic valve 10 can be positioned in the annulus 84 of a native heart valve 86 (e.g., the aortic valve) using the delivery assembly 100. When the surgeon determines that the native leaflets 88 are appropriately positioned in the leaflet-receiving regions 82, the prosthetic valve 10 can be expanded using the delivery assembly 100 such that the leaflet clamps 66 move from the open position shown in FIG. 10 to the closed position shown in FIG. 11 to clamp the leaflets 88 against the frame 12.

In alternative embodiments, the leaflet clamps 66 can comprise a single member instead of two strut members 68 coupled together. For example, in certain embodiments, the leaflet clamps 66 can comprise a single strut member that is curved such that it is U-shaped or V-shaped similar to the leaflet clamps 66. Such a strut member can be made from, for example, any of various shape-memory alloys such that the strut member can be crimped, and can spring back to its functional shape upon expansion of the frame. In yet further configurations, the leaflet clamps 66 can comprise a single straight strut member similar to the strut members 68 that is configured to move between the open position and the closed position together with the frame 12. In certain embodiments, the leaflet clamps 66 can also include any of a variety of atraumatic coverings, such as woven or nonwoven fabric, any of various electrospun coatings, etc., such as described below with reference to FIG. 17.

The leaflet clamp embodiments described herein can provide significant advantages over known prosthetic valve docking mechanisms. For example, because the leaflet clamps are part of the frame, a separate docking member and the associated delivery apparatus are not required. Additionally, because the leaflet clamps are actuated between the open and closed positions by motion of the frame between the contracted and expanded configurations, the leaflet clamps can be easily reopened and the prosthetic valve repositioned until the surgeon is satisfied with the placement of the prosthetic valve. An associated advantage of the mechanically expandable frame is that a balloon is not required to expand the frame to its functional size and, thus, there is no occlusion of blood flow during valve expansion. Also, because the leaflet clamps are actuated by motion of the prosthetic valve rather than by being self-expanding, the leaflet clamps need not be made from super-elastic or shape memory materials. Instead, the strut members forming the clamps can be made from relatively stronger and/or stiffer materials, such as stainless steel or cobalt-chromium alloys. In use, the strut members of the clamps are deformed within their elastic range when the frame is radially expanded and collapsed to move the clamps between their open and closed positions.

Additionally, although the illustrated configuration is adapted for implantation in the aortic valve, the frame and leaflet clamps can also be configured for implantation in the mitral valve and/or the tricuspid valve. For example, by reversing the orientation of the leaflet clamps 66 such that the first end portions 70 of the strut members 68 are coupled to the apices 24 at the lower end 16 of the frame (e.g., the outflow end of the frame when implanted at the mitral valve position), the leaflet clamps can be configured for use with the mitral valve and/or the tricuspid valve.

Figure 13:
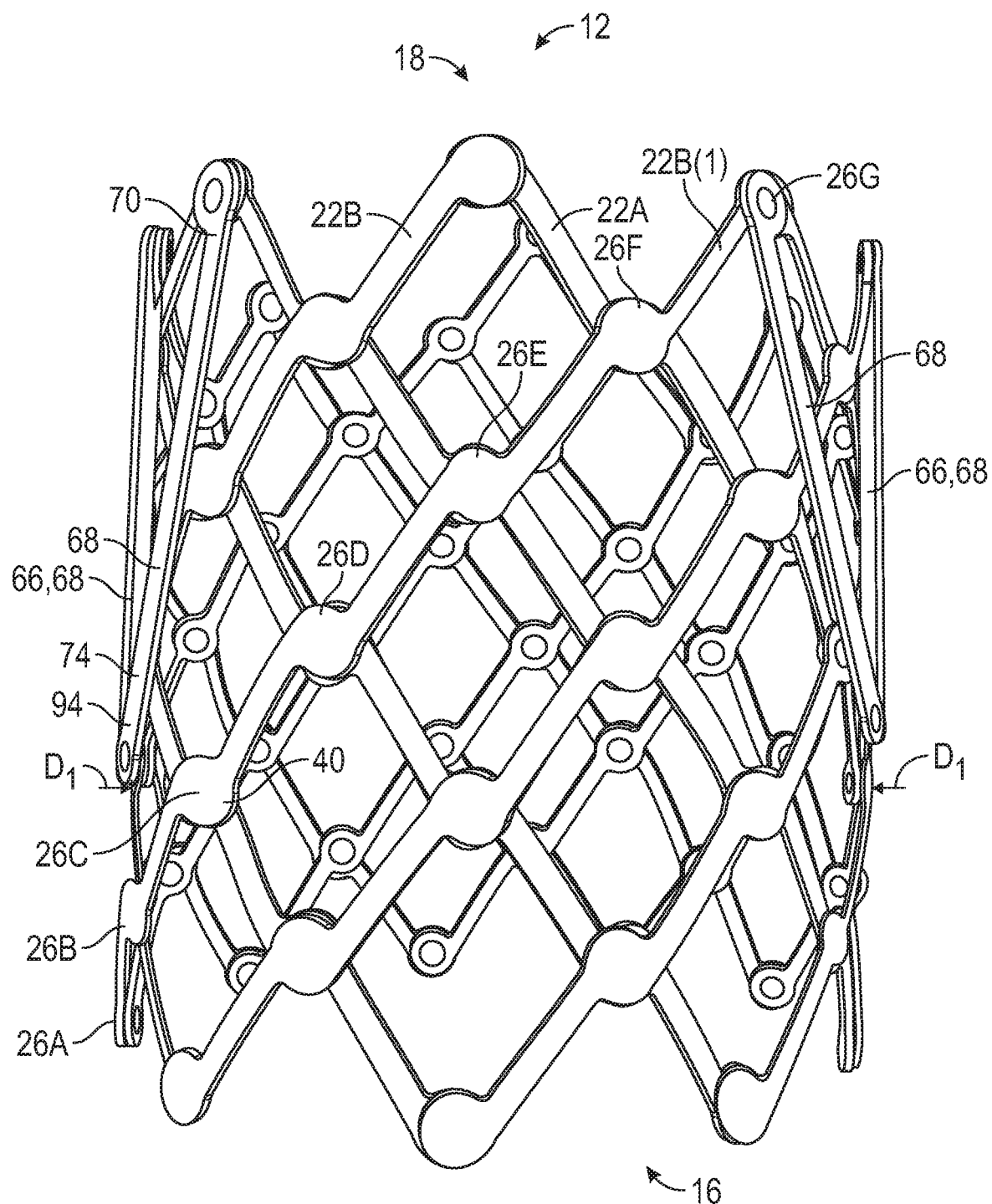
FIG. 13 is a side elevation view of another embodiment of a frame including inner strut members, outer strut members, and leaflet clamps, at a natural diameter of the frame.
Figure 14:
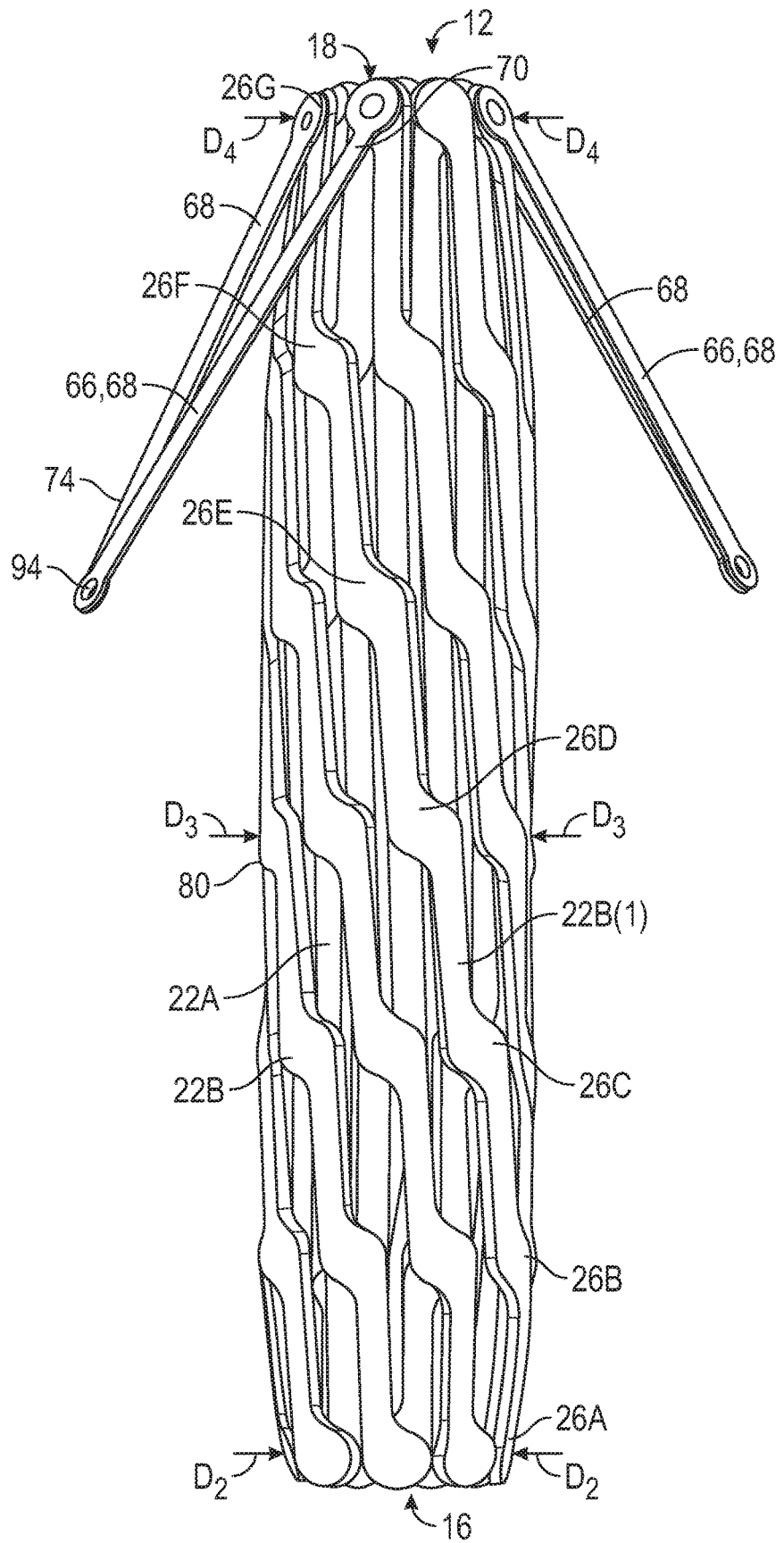
FIG. 14 is a side elevation view of the frame of FIG. 13 in the collapsed configuration with the leaflet clamps in the open position.
Figure 15:
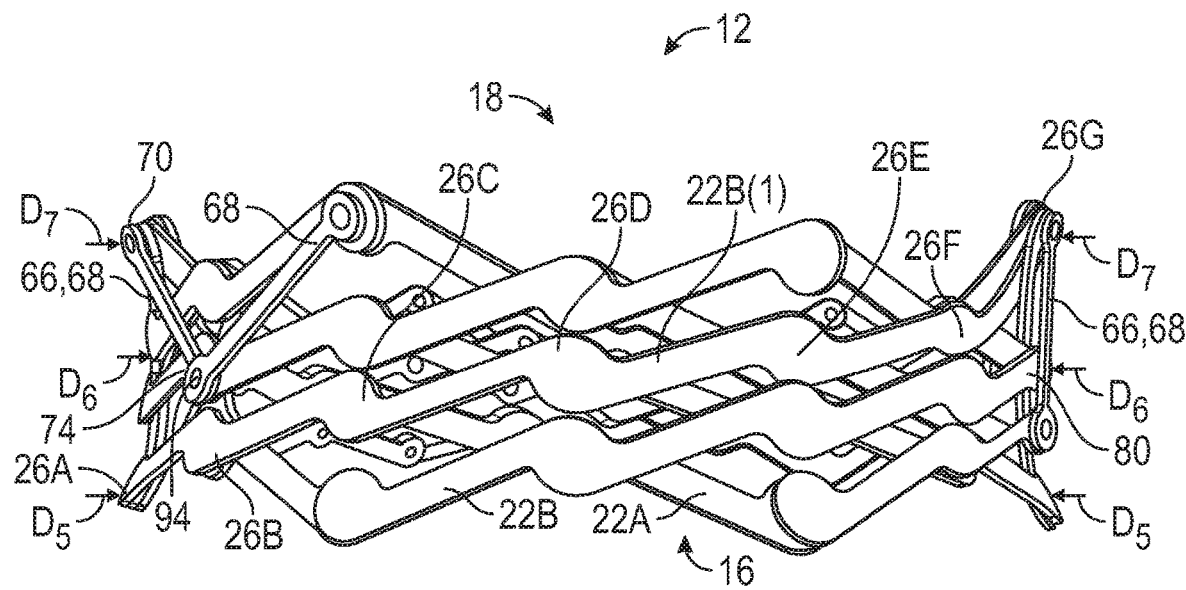
FIG. 15 is a side elevation view of the frame of FIG. 13 in the expanded configuration with the leaflet clamps in the closed position.

FIGS. 13-15 illustrate the frame 12 at various states of expansion including both the inner struts 22A and the outer struts 22B, as well as the leaflet clamps 66. FIG. 13 illustrates the frame 12 at its natural diameter $D_1$. Referring to a representative outer strut member 22B(1) for purposes of illustration, in the configuration shown the strut members can include seven round intermediate segments or portions 40. The intermediate portions 40 can be part of seven corresponding hinges or joints 26A-26G coupling together the outer strut member 22B(1) with the inner strut members 22A. The first end portions 70 of the struts 68 can be coupled to joints 26G at the outflow end 18 of the frame. At its natural diameter shown in FIG. 13, the struts 68 of the leaflet clamps 66 can lie parallel with and/or contact the outer strut members 22B of the frame.

FIG. 14 illustrates the frame 12 crimped to the collapsed configuration for delivery. In the collapsed configuration, both the inner and outer struts 22A, 22B can curve radially inwardly at the end portions of the frame. For example, the struts 22A and 22B can curve radially inwardly beginning from about the location of the joints 26B at the inflow end 16 of the frame and moving in an upstream direction toward the joints 26A. Likewise, the struts 22A and 22B can curve radially inwardly at their opposite ends beginning approximately at the joints 26F and moving in a downstream direction toward the joints 26G at the outflow end 18 of the frame. Thus, the inflow end 16 of the frame 12 at the level of the joints 26A can have a diameter $D_2$, and the outflow end of the frame at the level of the joints 26G can have a diameter $D_4$ that may be approximately equal to the diameter $D_2$. The diameters $D_2$ and $D_4$ can both be less than a diameter $D_3$ of the central portion 80 of the frame. For example, in certain embodiments the frame 12 can have the diameter $D_3$ from approximately the level of the joints 26B to approximately the level of the joints 26F such that the frame has a barrel-shaped profile. Because the struts 22A and 22B curve radially inward beginning at the joints 26F, the struts 68 of the leaflet clamps 66, which are coupled to the frame at the joints 26G, can be angled away from the frame in the open position.

FIG. 15 shows the frame 12 expanded to the expanded configuration. The frame 12 can have an hourglass-shaped profile in which the joints 26A and 26G are disposed radially outwardly of the joints 26B-26F therebetween. In this configuration, the frame can have a diameter $D_5$ at the joints 26A at the inflow end 16, and a diameter $D_7$ at the joints 26G at the outflow end 18. The central portion 80 can have a minimum diameter $D_6$ located approximately between the joints 26C and 26D. Because the strut members 22A and 22B twist, curve, or flare radially outwardly at the inflow and outflow ends of the frame, the struts 68 of the leaflet clamps 66 can be angled inwardly toward the frame. This can allow the leaflet clamps 66 to clamp the leaflets of a native heart valve against the exterior of the frame, as described above. In other embodiments, the strut members 22A and/or 22B can curve radially inwardly at locations other than the joints 26B and 26F. For example, in other embodiments the strut members 22A and/or 22B can curve radially inwardly at the joints 26C and 26E. In still other embodiments, the frame 12 can be configured such that the outflow end 18 curves radially inwardly in the collapsed configuration and radially outwardly in the expanded configuration to actuate the leaflet clamps, while the struts at the inflow end 16 exhibit little or no curvature, or remain parallel.

Figure 16:
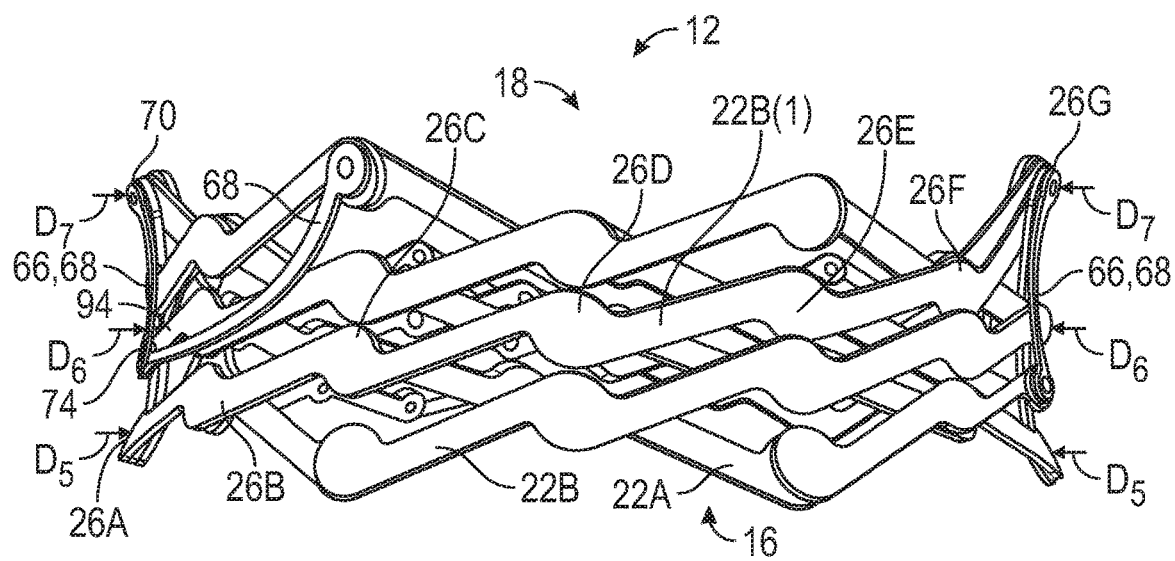
FIG. 16 is a side elevation view of the frame of FIG. 13 in the expanded configuration with the leaflet clamps in the closed position, and curved to correspond the curvature of the outer profile of the frame.

FIG. 16 illustrates another embodiment of the frame 12 in the expanded configuration in which the strut members 68 of the leaflet clamps are configured to curve along the outer surface of the frame in a direction from the outflow end 18 toward the inflow end 16. More particularly, the strut members 68 can be bowed or curved such that a concave side of the leaflet clamps 66 is oriented radially away from the longitudinal axis of the frame, and a convex side of the leaflet clamps is disposed adjacent or against the outer strut members 22B.

Figure 17:
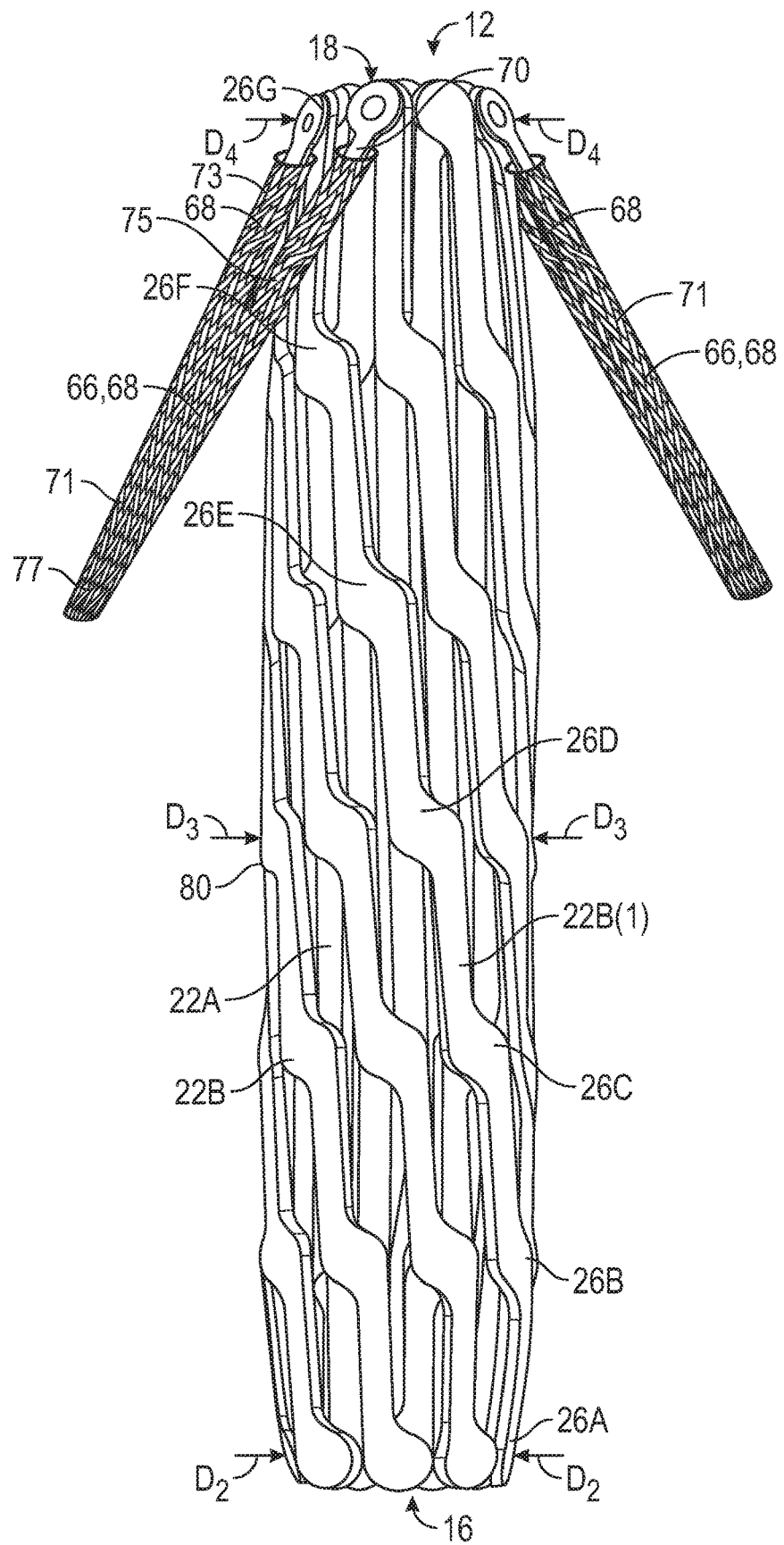
FIG. 17 is a side elevation view of the frame of FIG. 13 illustrating coverings disposed on the leaflet clamps.

FIG. 17 illustrates the frame 12 including coverings 71 disposed on the strut members 68 of the leaflet clamps 66. The coverings 71 can comprise tubular bodies in which the struts 68 can be received. In the illustrated embodiment, the coverings 71 comprise a first tubular portion 73 and a second tubular portion 75 that are in communication with a common third tubular portion 77 such that the coverings correspond to the V-shape of the leaflet clamps 66. In other embodiments, the coverings 71 can comprise a liner with a single lumen or opening configured to receive both struts of a leaflet clamp 66, or separate liner members configured to receive individual struts 68 of each leaflet clamp. The coverings can comprise a woven or non-woven fabric, a knitted fabric, and/or may comprise a polymeric layer, such as a dip-coated silicone layer or sleeve, or an electrospun expanded polytetrafluoroethylene (ePTFE) layer. The coverings may also comprise natural tissue. As noted above, the coverings 71 can provide cushioning to protect the native valve leaflets clamped between the leaflet clamps 66 and the frame 12, and/or to reduce the risk of injury to surrounding tissue. The coverings 71 can be configured to allow the leaflet clamps 66 to move between the open and closed positions as the frame expands and collapses. Such coverings may also be applied to the struts 22 of the frame, and/or about the frame as a whole. Representative frame coverings that may be used in combination with the frames described herein can be found in U.S. Publication No. 2018/0206982, and in U.S. Application Ser. No. 16/252,890, filed on Jan. 21, 2019, which are incorporated herein by reference.

Explanation of Terms

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

Unless otherwise indicated, all numbers expressing dimensions, quantities of components, angles, molecular weights, percentages, temperatures, forces, times, and so forth, as used in the specification or claims, are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

The invention claimed is:

1. A frame for a prosthetic heart valve, comprising:
a plurality of strut members arranged to form an annular main body of the frame and coupled together by a plurality of pivot joints, the main body of the frame being radially collapsible to a collapsed configuration and radially expandable to an expanded configuration, the main body of the frame having an inflow end and an outflow end; and
a plurality of leaflet clamps disposed on an exterior of the main body of the frame and coupled to the strut members, the plurality of leaflet clamps being movable between an open position corresponding to the collapsed configuration of the main body of the frame and a closed position corresponding to the expanded configuration of the main body of the frame; and wherein the leaflet clamps each comprise a pair of strut members pivotably coupled to the strut members of the main body of the frame
wherein motion of the main body of the frame between the collapsed configuration and the expanded configuration causes corresponding motion of the leaflet clamps between the open position and the closed position; and
wherein when the frame is in the collapsed configuration, central portions of the strut members are offset radially outwardly from respective inflow end portions and outflow end portions of the strut members with respect to a longitudinal axis of the frame such that the main body of the frame has a barrel-shaped profile.

2. The frame of claim 1, wherein:
the leaflet clamps comprise a first end portion coupled to the main body of the frame and a free second end portion; and
when the leaflet clamps are in the open position, the free second end portions are spaced radially outwardly from the main body of the frame.

3. The frame of claim 2, wherein when the leaflet clamps are in the closed position, the free second end portions are disposed adjacent the main body of the frame.

4. The frame of claim 1, wherein:
the strut members have respective inflow end portions located at the inflow end of the main body of the frame, respective outflow end portions located at the outflow end of the main body of the frame, and respective central portions between the inflow end portions and the outflow end portions; and
when the frame is in the expanded configuration, the central portions of the strut members are offset radially inwardly from the inflow end portions and from the outflow end portions of the strut members relative to a longitudinal axis of the frame such that the main body of the frame has an hourglass-shaped profile.

5. The frame of claim 1, wherein:
the strut members of the leaflet clamps each comprise a first end portion and a second end portion; and
when the leaflet clamps are in the open position, the second end portions of the strut members of the leaflet clamps are spaced radially outwardly from the main body of the frame.

6. The frame of claim 5, wherein the second end portions of the strut members of each leaflet clamp are coupled to each other such that the leaflet clamps are V-shaped when the frame is in the expanded configuration.

7. The frame of claim 5, wherein the first end portions of the strut members of the leaflet clamps are coupled to apices of the outflow end of the main body of the frame.

8. A prosthetic heart valve, comprising:
the frame of claim 1; and
a leaflet structure disposed at least partially within the frame.

9. The frame of claim 1, wherein the plurality of leaflet clamps comprise coverings.

10. A frame for a prosthetic heart valve, comprising:
a plurality of strut members arranged to form an annular main body, the main body of the frame being radially collapsible to a collapsed configuration and radially expandable to an expanded configuration, the main body of the frame having an inflow end and an outflow end and defining a longitudinal axis;
wherein the strut members of the frame have respective inflow end portions located at the inflow end of the main body, respective outflow end portions located at the outflow end of the main body, and respective central portions between the inflow end portions and the outflow end portions; and wherein when the frame expands to the expanded configuration, the central portions of the strut members are offset radially inwardly from the inflow end portions and from the outflow end portions of the strut members relative to the longitudinal axis such that the main body of the frame has an hourglass-shaped profile; and wherein when the main body of the frame collapsed to the collapsed configuration, the central portions of the strut members are offset radially outwardly from the respective inflow end portions and outflow end portions of the strut members with respect to the longitudinal axis of the frame such that the main body of the frame has a barrel-shaped profile.

11. The frame of claim 10, further comprising a plurality of leaflet clamps disposed on the exterior of the main body of the frame and coupled to the strut members.

12. The frame of claim 11, wherein the leaflet clamps are movable between an open position corresponding to the collapsed configuration of the main body of the frame and a closed position corresponding to the expanded configuration of the main body of the frame.

13. The frame of claim 11, wherein the leaflet clamps each comprise a pair of strut members pivotably coupled to the strut members of the main body of the frame.

14. The frame of claim 13, wherein:
the strut members of the leaflet clamps each comprise a first end portion and a second end portion; and
when the leaflet clamps are in an open position, the second end portions of the strut members of the leaflet clamps are spaced radially outwardly from the main body of the frame.

15. The frame of claim 14, wherein the second end portions of the strut members of each leaflet clamp are coupled to each other such that the leaflet clamps are V-shaped when the frame is in the expanded configuration.

16. The frame of claim 11, wherein the leaflet clamps are bowed when the frame is in the expanded configuration.

17. The frame of claim 10, wherein the strut members of the main body of the frame are coupled together by a plurality of pivot joints.

18. A prosthetic heart valve, comprising:
the frame of claim 10; and
a leaflet structure disposed at least partially within the frame.

19. A method of implanting a prosthetic heart valve, comprising:
advancing a prosthetic heart valve in a collapsed configuration to a native heart valve using a delivery apparatus, the prosthetic heart valve comprising a plurality of strut members coupled together by a plurality of pivot joints and arranged to form a frame having an annular main body, the main body of the frame being radially collapsible to the collapsed configuration and radially expandable to an expanded configuration, the frame including a plurality of leaflet clamps disposed on the exterior of the main body of the frame and coupled to the strut members, the leaflet clamps being movable between an open position corresponding to the collapsed configuration of the main body of the frame and a closed position corresponding to the expanded configuration of the main body of the frame;
positioning the prosthetic heart valve such that leaflets of the native heart valve are located between respective leaflet clamps and the main body of the frame; and
radially expanding the prosthetic heart valve from the collapsed configuration to the expanded configuration such that the leaflet clamps move from the open position to the closed position and clamp the leaflets against the prosthetic heart valve.

20. The method of claim 19, wherein:
the leaflet clamps comprise first end portions coupled to an outflow end of the main body of the frame and free second end portions; and
radially expanding the prosthetic heart valve further comprises expanding the main body of the frame beyond a natural diameter of the strut members such that the outflow end of the main body of the frame moves radially outwardly of a central portion of the main body of the frame and the free second end portions of the leaflet clamps move adjacent the main body of the frame.

* * * * *